United States Patent
Badley et al.

(10) Patent No.: US 8,093,234 B2
(45) Date of Patent: Jan. 10, 2012

(54) METHOD OF INCREASING THYMIC OUTPUT IN HIV-NEGATIVE PATIENTS BY TREATMENT WITH ANTIRETROVIRAL AGENTS

(75) Inventors: Andrew D. Badley, Rochester, MN (US); Stacey A. R. Vlahakis, Rochester, MN (US)

(73) Assignee: Mayo Foundation For Medical Education and Research, Rochester, MN (US)

( * ) Notice: Subject to any disclaimer, the term of this patent is extended or adjusted under 35 U.S.C. 154(b) by 84 days.

(21) Appl. No.: 11/580,359

(22) Filed: Oct. 13, 2006

(65) Prior Publication Data

US 2007/0219184 A1 Sep. 20, 2007

Related U.S. Application Data

(60) Provisional application No. 60/726,873, filed on Oct. 14, 2005.

(51) Int. Cl.
*A01N 43/00* (2006.01)
*A61K 31/33* (2006.01)

(52) U.S. Cl. ..................................... 514/183

(58) Field of Classification Search .................. None
See application file for complete search history.

(56) References Cited

PUBLICATIONS

Graham et al. Increased thymic output in HIV-negative patients after antiretroviral therapy. AIDS, 2005, vol. 19, No. 14, 1467-1472.*
Puro. et al. Effect of Antiretroviral agents on T-lymphocyte subset counts in healthy HIV-negative individuals. Journal of Immune Deficiency Syndrome. 24: 440-443.*
Hazenberg et al. Thymic output: a bad TREC record. Nature Immunology, vol. 4, No. 2, 2003.*
Radiology News. Nelfinavir added to chemotherapy shows promise for pancreatic cancer. Nov. 30, 1999. http://www.medicexchange.com/Radiology-Articles/nelfinavir-added-to-chemotherapy-shows-promise-for-pancreatic-cancer.html.*
S. A. Rizza, et al., "Nelfinavir monotherapy increases naïve T-cell numbers in HIV-negative healthy young adults", 2008, Frontiers in Biosceince, 13:1605-1609.
C. L. Cooper, et al., "Antiretroviral therapy influences cellular susceptibility to apoptosis in vivo", 2004, Frontiers in Bioscience, 9:338-341.
D.B. Graham, et al., "Increased thymic output in HIV-negative patients after antiretroviral therapy", 2005, AIDS, 19:1467-1472.
Badley, In vitro and in vivo effects of HIV protease inhibitors on apoptosis. Cell Death Differ. 2005;12 Suppl 1:924-31.
Badley et al., Dynamic correlation of apoptosis and immune activation during treatment of HIV infection. Cell Death Differ. 1999;6(5):420-32.
Chu et al., Exogenous IL-7 increases recent thymic emigrants in peripheral lymphoid tissue without enhanced thymic function. Blood. Aug. 15, 2004;104(4)1110-9.

Ferrando-Martinez et al., A reliable and simplified sj/beta-TREC ratio quantification method for human thymic output measurement. J Immunol Methods. 2010 352:111-117.
Hisatomi et al., HIV protease inhibitors provide neuroprotection through inhibition of mitochondrial apoptosis in mice. J Clin Invest. 2008;118(6):2025-38.
Kravcik et al., Comparative CD4 T-cell responses of reverse transcriptase inhibitor therapy with or without nelfinavir matched for viral exposure. HIV Clin Trials. 2001;2(2):160-70.
Singh et al., Nelfinavir/ritonavir reduces acinar injury but not inflammation during mouse caerulein pancreatitis. Am J Physiol Gastrointest Liver Physiol. 2009; 296(5):G1040-6.
Morinishi et al. Identification of severe combined immunodeficiency by T-cell receptor excision circles quantification using neonatal guthrie cards. J Pediatr. 2009;155(6):829-833.
Phenix et al., Decreased HIV-associated T cell apoptosis by HIV protease inhibitors. AIDS Res Hum Retroviruses. 2000;16(6):559-67.
Phenix et al., Antiapoptotic mechanism of HIV protease inhibitors: preventing mitochondrial transmembrane potential loss. Blood. 2001;98(4):1078-85.
Prelog et al., Thymectomy in early childhood: Significant alterations of the CD4+CD45RA+CD62L+T cell compartment in later life, Clin lmmunol. 2009;130(2):123-32.
Rizza and Badley, HIV protease inhibitors impact on apoptosis. Med Chem. 2008;4(1):75-9.
Routes et al., Statewide newborn screening for severe T-cell lymphopenia. JAMA. 2009; 302(22):2465-70.
Sportes et al., Administration of rhIL-7 in humans increases in vivo TCR repertoire diversity by preferential expansion of naive T cell subsets. J Exp Med. 2008 7;205:1701-1714.
Vlahakis et al., Flying in the face of resistance: antiviral-independent benefit of HIV protease inhibitors on T-cell survival. Clin Pharmacol Ther. 2007;82(3):294-9.
Vlahakis et al., HIV protease inhibitors modulate apoptosis signaling in vitro and in vivo. Apoptosis. 2007;12(5):969-77.
Weaver et al., Improved survival in experimental sepsis with an orally administered inhibitor of apoptosis. FASEB J. 2004;18(11):1185-91.
Weaver et al., Inhibition of adenine nucleotide translocator pore function and protection against apoptosis in vivo by an HIV protease inhibitor. J Clin Invest. 2005;115(7):1828-38.
Cunningham-Rundles et al., Clin Exp Immunol. 1999; 116:322-325.
Freier et al., Arch Dis Child. 1998; 78:371-372.
Hubert et al., International Immunology. 12(4):449-457, 2010.
Hazenberg et al., Blood. Jul. 15, 2006; 108 (2) 763-769.
Haynes et al., J. Clin Invest. Mar. 1999; 103(6):921.
Haynes et al., J Clin Invest. Feb. 1999; 103(4):453-60.
Lee et al., AIDS. Mar. 21, 2006; 20(5):667-74.
Delgado et al. J Infect Dis. Aug. 1, 2002; 186(3):410-4. Epub Jul. 5, 2005.
Westrop et al., PLoS One. 2009; 4(5):e5474. Epub May 12, 2009.
Ribeiro et al., J Acquir Immune Defic Syndr. Sep. 1, 2008; 49(1):1-8.

(Continued)

*Primary Examiner* — Brandon Fetterolf
*Assistant Examiner* — Anna Pagonakis
(74) *Attorney, Agent, or Firm* — Quarles & Brady, LLP

(57) ABSTRACT

A method of increasing thymic output in an HIV-negative patient, comprising the steps of (a) identifying a HIV-negative patient who is in need of increased thymic output and (b) supplying an effective amount of antiretroviral agent to the patient such that the patient has an increase in naïve T-cells.

13 Claims, 2 Drawing Sheets

PUBLICATIONS

Fernandez et al., AIDS Res Hum Retroviruses. Feb. 2006; 22(2):163-70.
Cohen et al., AIDS. Nov. 22, 2002; 16(17):2263-6.
McFarland et al., Proc Natl Acad Sci USA. Apr. 11, 2000; 97(8):4215-20.
Steffens et al., Clin Immunol. Nov. 2000; 97(2):95-101.
Weinberg et al., Blood. Mar. 1, 2001; 97(5):1458-66.
Steffens et al., AIDS. Sep. 28, 2001; 15(14):1757-64.
Kolte et al., J Infect Dis. Jun. 1, 2002;185(11); 1578-85. Epub May 17, 2002.
Fry et al., Blood. Mar. 15, 2003; 101(6):2294-9. Epub Oct. 31, 2002.
Pham et al., Clin Diagn Lab Immunol. Mar. 2003; 10(2):323-8.
Carcelain et al., AIDS. Apr. 11, 2003;17(6):841-50.
Mancebo et al., Clin Exp Immunol. Dec. 2008; 154(3):375-83. Epub Sep. 22, 2008.
Sempowski et al., J Immunol. Feb. 15, 2001; 166(4):2808-17.
Teixera et al., AIDS. Sep. 2001; 15(14):1749-1756.
Ruiz-Mateos et al., AIDS. May 2003; 17(7):947-954.
Ometto et al., AIDS. Apr. 2002; 16(6):839-849.
De Rossi et al., J. Infect Dis. Aug. 2002; 186(3):312-320.
Andre et al., Proc Natl Acad Sci U S A. Oct. 1998; 95(22):13120-13124.
Sgadari et al., Nat Med. Mar. 2002; 8(3):225-232.
Dewan et al., Blood. Jan. 2006; 107(2):716-724.
Ghibelli et al., Biochem Pharmacol. Oct. 2003; 66(8):1505-1512.
Atzori et al., J. Infect Dis. May 2000; 181(5):1629-1634.
Cassone et al., J. Infect Dis. Aug. 1999; 180(2):448-453.
Pati et al., Blood. May 2002; 99(10):3771-3779.
Kong et al., Immunity. Jan. 1998; 8(1):97-104.
Zediak et al., Semin Immunol. Oct. 2005; 17(5):337-346.
Al-Harthi et al., J. Immunol Methods. Apr. 2000; 237(1-2):187-197.
Douek et al., Nature. Dec. 1998; 396(6712):690-695.
Naylor et al., J. Immunol. Jun. 2005; 174(11):7446-7452.
Dare et al., J. Immunol Methods. Jan. 2006; 308(1-2):1-12.
Hadrup et al., J. Immunol. Feb. 2006; 176(4):2645-2653.
Goronzy et al., Curr Opin Immunol. Oct. 2005; 17(5):468-475.
Taub et al., Immunol Rev. Jun. 2005; 205:72-93.
Baba et al., Parkinsonism Relat Disord. Dec. 2005; 11(8):493-498.
Phillips et al., J. Immunol. Oct. 2004; 173(8):4867-4874.
Murphy et al., J Immunol. Dec. 1992; 149(12):3851-3857.
Montecino-Rodriguez et al., Endocrinology. Oct. 1998; 139(10):4120-4126.
Puro et al., JAIDS. 2000; 24:440-443.
Signorini et al., Br. Journal of Haematology. 2000; 110:434-437.
Laurence et al., J. Clin. Invest. Feb. 1996; 97(3):672-680.

\* cited by examiner

METHOD OF INCREASING THYMIC OUTPUT IN HIV-NEGATIVE PATIENTS BY TREATMENT WITH ANTIRETROVIRAL AGENTS

CROSS REFERENCE TO RELATED APPLICATIONS

This application claims the benefit of U.S. provisional 60/726,873, filed on Oct. 14, 2005, incorporated by reference as if fully set forth herein.

STATEMENT REGARDING FEDERALLY SPONSORED RESEARCH OR DEVELOPMENT

BACKGROUND OF THE INVENTION

Highly active antiretroviral therapy (HAART) has altered the course of Human Immunodeficiency Virus (HIV) infection. Treatment with a combination of nucleoside analogs and protease inhibitors results in profound inhibition of HIV replication, as well as quantitative and qualitative improvements in host immune function. T-cell counts increase to varying degrees in patients on HAART therapy. The increase in CD4+ T cells may result from homeostatic expansion of existing T-cells, as well as production of new T-cells from the thymus. Several groups have reported that HIV-infected individuals receiving HAART produce thymic-derived naïve T-cells, as determined by T-cell receptor (TCR) excision circles (TREC).[1-4] However, it remains unclear whether HAART increases thymic T-cell output by reducing the pathogenic effects of HIV on the thymus, or by a direct drug effect on the thymus.

A recent report demonstrated an increase in TREC-positive cells from the peripheral blood of HIV-negative health-care workers who received nelfinavir, Zidovudine, and Lamivudine HAART for 28 days for post-HIV-exposure prophylaxis (PEP),[5] raising the possibility that HAART may directly impact thymic output.

Increasing evidence suggests that HIV protease inhibitors may have intrinsic immunomodulatory activity. These effects include inhibition of proteasome function,[6] anti-tumor effects in models of Kaposi's sarcoma,[7] reduced cellular activation associated with inhibited NF-κB activation,[8] direct inhibition of calpain,[9] matrix metalloprotinease,[7] and aspartyl proteases produce by PCP,[10] and Candida,[11] as well as anti-apoptotic effects.[12] These effects also occur in vivo, since mice implanted with Kaposi's sarcoma and treated with Ritonavir experience significant tumor regression and NOD/SCID mice implanted with adult T-cell leukemia cells experience reduced tumor growth in the presence of Ritonavir.[8, 13] In addition, treatment of mice with nelfinavir/Ritonavir reduces mortality due to poly-microbial sepsis,[14] Fas-induced hepatitis,[15] SEB/D-gal induced shock[15] and reduces neuronal injury due to cerebral ischemia.[15]

Needed in the art of disease treatment is a method of increasing the number of naïve T-cell numbers in an HIV-negative patient using protease inhibitors.

BRIEF SUMMARY OF THE INVENTION

A principal function of the thymus is to produce naïve T-cells, which can be recognized in the periphery by the presence of T-cell receptor excision circles (TREC).[16] Upon entry to the thymus, bone marrow derived CD34+ progenitors interact with the thymic stroma and undergo a series of maturation events which requires both activation, as well as the selective induction of apoptosis.[17] Since HIV PIs might impact both activation, as well as apoptosis, we hypothesized that the effect of HAART on naïve T-cell number might be due to the PI component of such therapy. Since increases in naïve T-cell numbers might occur through expansion of existing peripheral naïve cells or by de novo thymic production, there is no phenotypic marker which can be used to selectively identify recent thymic emigrant T-cells.[18] Instead, we specifically assessed the impact of nelfinavir on thymic derived naïve T-cell numbers in the peripheral blood in healthy volunteers by quantitating TREC/CCR5 copy levels.[19]

In one embodiment, the present invention is a method of increasing thymic output in an HIV-negative patient, comprising the steps of (a) identifying a HIV-negative patient who is in need of increased thymic output and (b) supplying an effective amount of antiretroviral agent to the patient such that the patient has an increase in naïve T-cells.

In a particularly preferred embodiment of the present invention, the patient has idiopathic CD4 lymphocytopenia. In another preferred version of the invention, the patient has received chemotherapy or bone marrow transplant.

Other objects, advantages and methods of the present invention will be apparent to one of skill in the art after review of the specification claims and drawings.

DESCRIPTION OF THE INVENTION

In General

Figure 1:
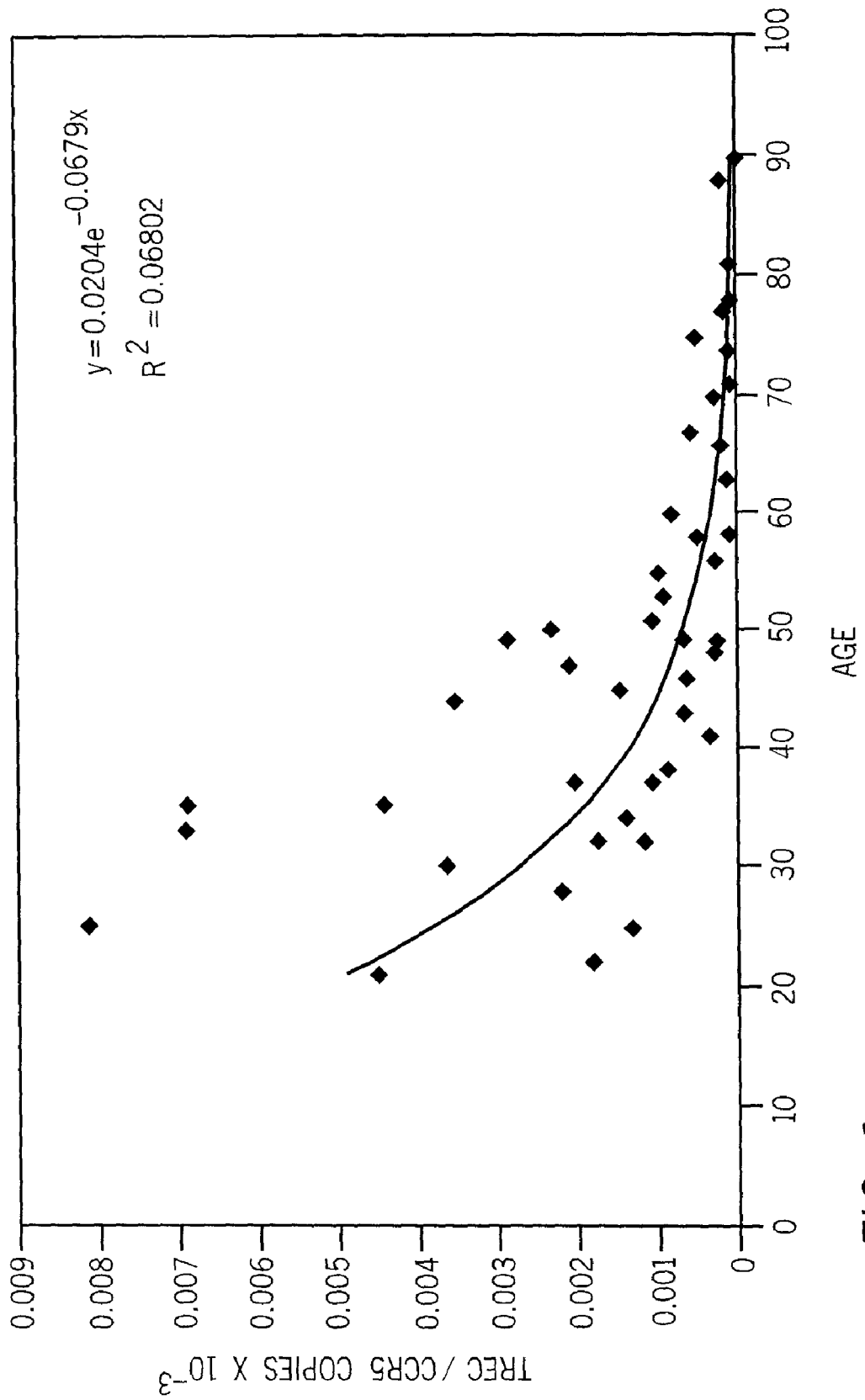
FIG. 1 is a graph disclosing that TREC levels decrease with advancing age. Baseline TREC/CCR5 copies were assessed from the peripheral blood of healthy adults. The results are plotted according to subject age.

In one embodiment, the present invention is a method of increasing thymic output in HIV-negative patients. In a preferred embodiment, the method comprises the step of administering an antiretroviral therapy (ART) to an HIV-negative patient and observing an increase in thymic output. By "thymic output" we mean an increase in naïve T-cells, preferably as measured by phenotypic markers and TCR recombination excision circles (TRECs), specifically signal joint (sj) TRECs.

Preferred Patient

The Example below is a disclosure of one preferred embodiment of the present invention. The Example analyzes TREC levels in forty six volunteers, ages 22 to 95 years old. Eight volunteers responded to ART therapy with increases in TREC numbers from base line to day 21, with a median increase of TRECs of 1.2 copies TREC/CCR5. Sub-group analysis demonstrated an age related association. The average increase in TREC levels for subjects less than 40 years was 1.2 TREC/CCR5 copies, for subjects 40-65 years was 0.80 TREC/CCR5 copies and the average change in TREC levels for subjects greater than 65 years was 0.89 TREC/CCR5 copies after ART. Therefore, the method of the present invention is expected to be more clinically useful to younger patients (less than 40 years old) but is expected to be clinically useful for some patients over 40 years old.

The method of the present invention will be particularly advantageous with HIV-negative patients in need of increased thymic output. Preferably, these patients would be characterized as follows: Patients who would be predicted to have impaired thymic output would include elderly, chronically ill, patients who have received or are receiving immunosuppressive medications including but not limited to chronic steroid administration, immunosuppressives related to organ transplantation, having received a bone marrow transplant or chemotherapy, certain surgical procedures such as thymectomy or splenectomy.

In another preferred version of the present invention, a patient has idiopathic CD4 lymphocytopenia.

Method of Increasing Thymic Output

In one embodiment, the present invention is a method of increasing thymic output in HIV-negative patients. As described above, one would first identify a patient in need of thymic output increase. One would then supply antiretroviral therapy to the HIV-negative patient.

In a preferred embodiment, we envision the use of nelfinavir mesylate, VIRACEPT, as the antiretroviral therapy. However, we envision that the present invention will be useful for any HIV protease inhibitor, such as AGENERASE (amprenavir), APTIVUS (tipranavir), CRIXIVAN (indinavir), INVIRASE (saquinavir), KALETRA (lopinavir & ritonavir), LEXIVA (fosamprenavir), NORVIR (ritonavir), PREZISTA (darunavir), and REYATAZ (atazanavir), as well as VIRACEPT (nelfinavir).

A preferable dose of nelvinavir is 1250 mg orally, twice a day for 21 days. We envision that one could modify this dosage and still obtain good results. For example, a dose of between 1000-2000 mg orally, twice a day for between 15 and 25 days is another preferred embodiment of the present invention. In general, one would supply the ART in the way recommended by manufacturers of the protease inhibitors.

One would wish to take a biological sample from the patient to determine if the treatment is successful. The Examples below demonstrate a determination at day 3, day 5, day 7, day 14 and day 21. One may also wish to obtain a sample at day 28. If the treatment is not producing the desired result by day 28, we believe that the therapy will not be successful.

Analysis of Treatment

In one embodiment, treatment of patients in the present invention will be as follows:

Blood will be sampled before therapy (time 0), preferably at day 3, day 5, day 7, day 14, and day 21. TREC Analysis: DNA will be isolated from peripheral blood lymphocytes (PBL) using an EASY DNA kit (Invitrogen) and assessed for signal joint (sj) TREC content relative to genomic CCR5 copies by real time PCR in a spectroflourometric thermal cycler (ABI PRISM 7700, PE Applied Biosystems). SjTREC reactions typically contain 25 pmol primers (forward CACATCCCTTTCMCCATGCT [SEQ ID NO:1]), reverse GCCAGCTGCAGGGTTTAGG [SEQ ID NO:2]) 125 nM TAQMAN probe (FAM-ACACCTCTGGTTTTTGTAAAG-GTGCCCACT-TAMRA [SEQ ID NO:3], 1× TAQMAN Universal PCR Master Mix (PE Applied Biosystems), and 60 ng of template DNA in a total volume of 50 ul. CCR5 reactions will typically contain 25 pmol primers (forward GTGT-CAAGTCCAATCTATGACATCAA [SEQ ID NO:4], reverse GCCTGCGATTTGCTTCACA [SEQ ID NO:5]), 125 nM TAQMAN probe (FAM-TATTATACATCGGAGC-CCTGCCAAAAAATCA-TAMRA [SEQ ID NO:6]), 1× TAQMAN Universal PCR Master Mix, and 60 ng of template DNA in a total volume of 50 ul. Thermal cycling conditions will typically consist of 2 minute incubation at 50° C. and an initial denaturation at 95° C. for 10 minutes, followed by 40 cycles of 95° C. for 10 minutes and 60° C. for 1 minute.

The genomic CCR5 copies are determined by real time PCR. These are used as a standard to reflect the number of PBLs are being evaluated. (See procedure in Examples.)

For each run, standard curves will be generated, typically with 1-100,000 copies of human sjTREC plasmid (see D. Douek, et al., Nature Dec. 17, 1998; 396 (6712): 690-695, incorporated by reference) or human CCR5 plasmid (cloned by RT-PCR into pCI) in order to calculate copies of TREC versus CCR5. TREC values will be expressed as TREC copy number per two copies of CCR5 or TREC/peripheral blood leukocytes (PBL).

Preferably, success of our treatment can be monitored in the following ways:

a) One might determine TREC number, immunophenotype number, or immune function by laboratory assay such as ELISPOT before and after therapy. In a successful result, one would expect to see increased TREC number, increased naïve T-cell count or increased ELISPOT response. One would expect to see the TREC measurement increase at least 1.2-3 fold, preferably at least 2-3 fold.

b) One might measure immune response to vaccine as assessed by antibody level and/or functional assays such as ELISPOT assays. In a successful outcome, one would expect to see increased antibody level and increased ELISPOT response.

c) One might measure disease incidence in patients who have received the treatment. For example, in patients receiving influenza vaccine with and without nelfinavir one would compare influenza incidence and all causes of mortality in patients receiving nelfinavir versus placebo.

d) Improved thymic output may beneficially impact disease outcome from certain malignancies. Thus, we envision treating patients with select malignancies (included, but not limited to, melanoma, lymphoma, leukemia, etc.) with protease inhibitors such as nelfinavir. Evaluating outcome of treatment would be compared by evaluating disease-free survival and mortality between patients receiving nelfinavir in addition to standard medical practice to patients receiving placebo in addition to standard medical practice.

EXAMPLES

In General

Although patients treated with HIV protease inhibitor (PI) containing regimens manifest increases in naïve T-cell number, it is unclear whether this is due to reduction in viral replication or a direct drug effect. We questioned whether nelfinavir mono-therapy directly impacted naïve T-cell number in HIV-negative individuals. HIV-negative volunteers received nelfinavir 1250 BID for 3 weeks, and T-cell receptor recombination excision circles (TREC) content in peripheral blood was assessed at baseline, during, and after 21 days of nelfinavir therapy in 15 subjects. TREC copies/copies CCR5 increased following nelfinavir mono-therapy in 8 patients ($p<0.02$), and did not change in 7 patients (p=NS). Those patients who responded were younger than those who did not with a median age of 55 years for responders and 71 years for non-responders ($p<0.03$). The increase in TREC was most pronounced in those patients less than 40 years old ($p<0.01$). Moreover, the patients who did not increase TREC levels were more likely to have suffered a medical illness previously shown to reduce thymic function.

In HIV-negative patients, mono-therapy with the HIV PI nelfinavir for 21 days increases TREC positive naïve T-cell number particularly in individuals who are healthy and/or young.

Methods

Following approval by the Mayo Institutional Review Board, peripheral blood was sampled from 46 healthy blood donors older than 18 years of age for baseline TREC analysis. For the separate nelfinavir trial, 15 HIV-negative individuals with no active illness older than 18 years of age were given nelfinavir, 1250 mg orally, twice a day for 21 days. Blood for TREC analysis was obtained before therapy and on days 3, 5, 7, 14, and 21 after starting therapy. At each blood draw, side-effects were monitored and recorded from each subject. Severity of diarrhea was graded as: Grade 0—None; Grade 1—increase of 4 stools/day over pretreatment; Grade 2—increase of 4-6 stools/day, or nocturnal stools; Grade 3—increase of 7 stools/day or incontinence, or dehydration episode requiring parenteral support; Grade 4—episode of hemodynamic collapse requiring intensive care.

TREC Analysis: DNA was isolated from peripheral blood mononuclear cells (PBMC) using an QIAamp Blood Mini DNA Kit (Qiagen) and assessed for signal joint (sj) TREC content relative to genomic CCR5 copies by real-time PCR in a spectroflourometric thermal cycler (ABI PRISM 7700 or 7900, PE Applied Biosystems). SjTREC reactions contained 12.5 pmol primers (forward CACATCCCTTTCAACCAT-GCT [SEQ ID NO:1]), reverse GCCAGCTGCAGGGTT-TAGG [SEQ ID NO:2]) 3 pmoles TAQMAN probe (FAM-ACACCTCTGGTTTTTGTAAAGGTGCCCACT-TAMRA [SEQ ID NO:3]), 1× TAQMAN Universal PCR Master Mix (PE Applied Biosystems), and 50 to 400 ng of template DNA in a total volume of 25 μl. CCR5 reactions contained 12.5 pmol primers (forward GTGTCMGTCCMTCTATGACAT-CAA [SEQ ID NO:4], and reverse GCCTGCGATTTGCT-TCACA [SEQ ID NO:5]), 3 pmoles TAQMAN probe (FAM-TATTATACATCGGAGCCCTGCCAAAAAATCA-TAMRA [SEQ ID NO:6]),1× TAQMAN Universal PCR Master Mix, and 50-400 ng of template of genomic DNA in a total volume of 25 μl. Thermal cycling conditions consisted of a 2-minute incubation at 50° C. and an initial denaturation/activation step at 95° C. for 10 minutes, followed by 40 cycles of 95° C. for 15 seconds and 60° C. for 1 minute in a microplate format. For each plate of reactions, standard curves were generated with 1-100,000 copies of human sjTREC plasmid (provided by Dr. D. Douek, NIH) and human CCR5 plasmid (cloned by RT-PCR into pCI) in order to calculate copies of TREC versus CCR5.

Statistical analysis: Experiments from every figure were performed in duplicate and repeated at least twice. All measurements are presented as means and standard deviations with statistical comparisons made between baseline and day 21 TREC/CCR5 measurements using the Student's t test for paired observations. For FIG. 2, change in baseline to day 21 TREC/CCR5 levels were stratified according to subjects age with 2 subjects <40, 2 subjects 40-65, and 11 subjects >65 years old.

Results And Discussion

TREC levels were analyzed in 46 volunteers, ages 22-95 years old. Consistent with previous findings,[20] TREC level decreased with advancing subject age ($R^2=0.6802$) (FIG. 1). Fifteen HIV-negative adults, ages 22-95, were treated with nelfinavir, 1250 mg orally, twice a day for 21 days. nelfinavir mono-therapy was clinically well tolerated; six (40%) of the subjects experienced Grade 1 or 2 diarrhea, and all but one subject completed the 21 days of therapy. Compliance was good in all patients, as assessed by self-reporting and pill counts at the time of each blood draw.

Figure 2:
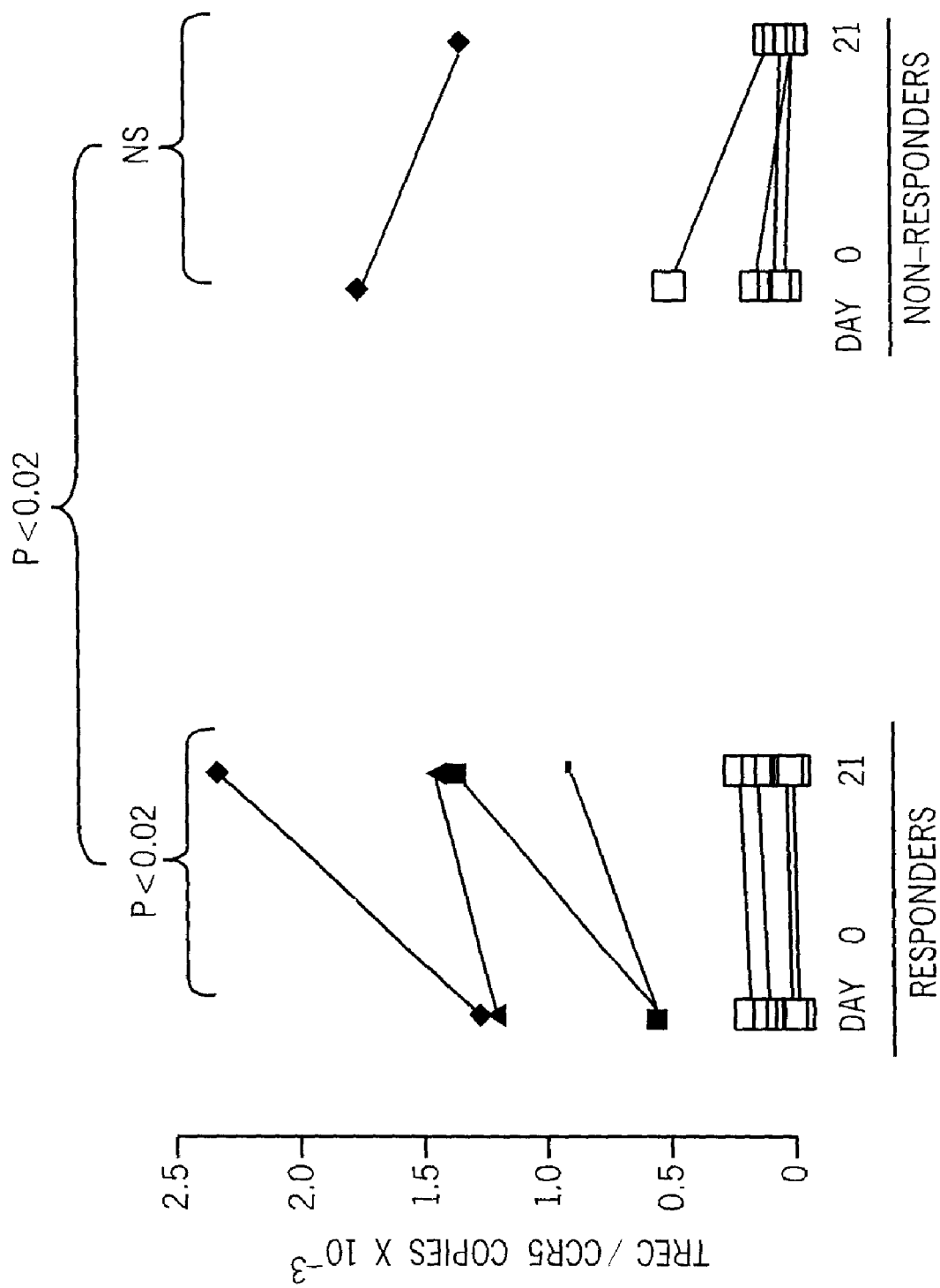
FIG. 2 is a graph disclosing that nelfinavir therapy induces an increase in TREC levels in a subset of healthy adults.

In order to establish if nelfinavir mono-therapy increased naïve T-cells after 21 days of treatment in adult subjects, a paired analysis of change in TREC levels from baseline to days 3, 5, 7, 14, and 21 were determined. In our previous report, TREC/CCR5 levels on T-cells did not alter over 21 days in an untreated control group of HIV-negative adults.[5] No significant change in TREC levels occurred below baseline (day 0) and days 3, 5, 7, or 14. After 21 days of therapy, although there was no change between baseline and day 21 TREC/CCR5 levels, when the entire cohort was analyzed, it was apparent that some subjects responded to nelfinavir therapy with increasing TREC/CCR5 copy levels. Since no patient in our control group had any increase in TREC levels over a 3 week period, we analyzed volunteers who increased TREC/CCR5 levels separately.[5] Eight volunteers (53% of total) responded to nelfinavir therapy with increases in TREC numbers from baseline to day 21, with a median increase in TRECs of 1.2 copies TREC/CCR5 ($p<0.02$). Conversely, 7 volunteers (47% of total) did not increase TREC numbers following 21 days of nelfinavir (FIG. 2).

Although only half of the subjects increased TREC/CCR5 levels after nelfinavir therapy, sub-group analysis demonstrated an age-related association. The average increase in TREC levels for subjects less than 40 was 1.2 TREC/CCR5 copies, for subjects 40-65 was 0.80 TREC/CCR5 copies and the average change in TREC levels for subjects greater than 65 was 0.89 TREC/CCR5 copies, after nelfinavir therapy. The median age of the responders was 55 years (range 23-90), whereas, the mean age of the non-responders was 71 years (range 37-88) ($p<0.03$), suggesting that age, and consequently, thymic reserve might determine thymic response to nelfinavir.

Our results confirm that the normal process of aging results in impaired thymopoiesis (FIG. 1) that may predispose to infections and cancers.[20-23] Moreover, aging associated impairments in thymopoiesis, and/or thymic reserve appear to influence thymic response to nelfinavir therapy. (FIG. 2) Younger compared to older individuals responded more robustly to nelfinavir, consistent with observations that aging is associated with reduced thymic stroma, size, function and output.[24]

The overlap in ages between nelfinavir responders and non-responders is likely reflective of aging independent causes of early thymic atrophy, including puberty, pregnancy, stress, exercise and trauma, as well as disease states including cancers, Diabetes, and Parkinson's disease (reviewed in [24]). Of note, 5 of the 7 non-responders had prior or chronic illness that may have decreased their thymic reserve, including prostate cancer, non-small cell lung cancer, Diabetes mellitus, and Parkinson's disease.[25] In contrast, only one of eight of the responders had a similar illness (Table 1). Increased understanding of thymic biology has led to cytokine and hormone-based approaches to reversing thymic involution in animal models using agents such as IL-7,[26] GH,[27] IGF-1.[28] Recognizing that HIV PI may also impact thymic function, offers new insights into potential therapies aimed at restoring thymic function in vivo. Moreover, the changes observed in this study confirm and highlight the direct immunologic effects of HIV PI therapy.

TABLE 1

| Subject | Age | Cancer | Chronic Disease | Day 21/0 TREC |
|---------|-----|--------|-----------------|---------------|
| 1 | 67 | Breast | | 2.32 |
| 2 | 88 | | | 1.88 |
| 3 | 71 | | Parkinson's disease | 0.59 |
| 4 | 75 | | | 0.29 |
| 5 | 77 | Prostate | | 0.38 |

TABLE 1-continued

| Subject | Age | Cancer | Chronic Disease | Day 21/0 TREC |
|---------|-----|--------|-----------------|---------------|
| 6 | 78 | | Diabetes Mellitus | 0.55 |
| 7 | 81 | | Parkinson's disease | 0.74 |
| 8 | 90 | | | 1.18 |
| 9 | 78 | Lung | | 0.24 |
| 10 | 63 | | | 1.25 |
| 11 | 74 | | | 1.01 |
| 12 | 36 | | | 0.72 |
| 13 | 26 | | | 1.0 |
| 14 | 23 | | | 1.36 |
| 15 | 33 | | | 1.06 |

REFERENCES

1. Teixeira L, Valdez H, McCune J M, et al. Poor CD4 T cell restoration after suppression of HIV-1 replication may reflect lower thymic function. *Aids*. Sep. 28, 2001; 15(14): 1749-1756.
2. Ruiz-Mateos E, de la Rosa R, Franco J M, et al. Endogenous IL-7 is associated with increased thymic volume in adult HIV-infected patients under highly active antiretroviral therapy. *Aids*. May 2, 2003; 17(7):947-954.
3. Ometto L, De Formi D, Patiri F, et al. Immune reconstitution in HIV-1-infected children on antiretroviral therapy: role of thymic output and viral fitness. *Aids*. Apr. 12, 2002; 16(6):839-849.
4. De Rossi A, Walker A S, Klein N, De Formi D, King D, Gibb D M. Increased thymic output after initiation of antiretroviral therapy in human immunodeficiency virus type 1-infected children in the Paediatric European Network for Treatment of AIDS (PENTA) 5 Trial. *J Infect Dis*. Aug. 1, 2002; 186(3):312-320.
5. Graham D B, Bell M P, Huntoon C J, et al. Increased thymic output in HIV-negative patients after antiretroviral therapy. *Aids*. Sep. 23, 2005; 19(14):1467-1472.
6. Andre P, Groettrup M, Klenerman P, et al. An inhibitor of HIV-1 protease modulates proteasome activity, antigen presentation, and T cell responses. *Proc Natl Acad Sci USA*. Oct. 27, 1998; 95(22):13120-13124.
7. Sgadari C, Barillari G, Toschi E, et al. HIV protease inhibitors are potent anti-angiogenic molecules and promote regression of Kaposi sarcoma. *Nat Med*. March 2002; 8(3): 225-232.
8. Dewan M Z, Uchihara J N, Terashima K, et al. Efficient intervention of growth and infiltration of primary adult T-cell leukemia cells by an HIV protease inhibitor, ritonavir. *Blood*. Jan. 15, 2006; 107(2):716-724.
9. Ghibelli L, Mengoni F, Lichtner M, et al. Anti-apoptotic effect of HIV protease inhibitors via direct inhibition of calpain. *Biochem Pharmacol*. Oct. 15, 2003; 66(8): 1505-1512.
10. Atzori C, Angeli E, Mainini A, Agostoni F, Micheli V, Cargnel A. In vitro activity of human immunodeficiency virus protease inhibitors against *Pneumocystis carinii*. *J Infect Dis*. May 2000; 181(5):1629-1634.
11. Cassone A, De Bernardis F, Torosantucci A, Tacconelli E, Tumbarello M, Cauda R. In vitro and in vivo anticandidal activity of human immunodeficiency virus protease inhibitors. *J Infect Dis*. August 1999; 180(2):448-453.
12. Phenix B N, Lum J J, Nie Z, Sanchez-Dardon J, Badley A D. Antiapoptotic mechanism of HIV protease inhibitors: preventing mitochondrial transmembrane potential loss. *Blood*. Aug. 15, 2001; 98(4): 1078-1085.
13. Pati S, Pelser C B, Dufraine J, Bryant J L, Reitz M S, Jr., Weichold F F. Antitumorigenic effects of HIV protease inhibitor ritonavir: inhibition of Kaposi sarcoma. *Blood*. May 15, 2002; 99(10):3771-3779.
14. Weaver J G, Rouse M S, Steckelberg J M, Badley A D. Improved survival in experimental sepsis with an orally administered inhibitor of apoptosis. *Faseb J*. August 2004; 18(11):1185-1191.
15. Weaver J G, Tarze A, Moffat T C, et al. Inhibition of adenine nucleotide translocator pore function and protection against apoptosis in vivo by an HIV protease inhibitor. *J Clin Invest*. July 2005; 115(7):1828-1838.
16. Kong F, Chen C H, Cooper M D. Thymic function can be accurately monitored by the level of recent T cell emigrants in the circulation. *Immunity*. January 1998; 8(1):97-104.
17. Zediak V P, Bhandoola A. Aging and T cell development: interplay between progenitors and their environment. *Semin Immunol*. October 2005; 17(5):337-346.
18. Al-Harthi L, Marchetti G, Steffens C M, Poulin J, Sekaly R, Landay A. Detection of T cell receptor circles (TRECs) as biomarkers for de novo T cell synthesis using a quantitative polymerase chain reaction-enzyme linked immunosorbent assay (PCR-ELISA). *J Immunol Methods*. Apr. 3, 2000; 237(1-2):187-197.
19. Douek D C, McFarland R D, Keiser P H, et al. Changes in thymic function with age and during the treatment of HIV infection. *Nature*. Dec. 17, 1998; 396(6712):690-695.
20. Naylor K, Li G, Vallejo A N, et al. The influence of age on T cell generation and TCR diversity. *J Immunol*. Jun. 1, 2005; 174(11):7446-7452.
21. Dare R, Sykes P J, Morley M, Brisco M J. Effect of age on the repertoire of cytotoxic memory (CD8+CD45RO+) T cells in peripheral blood: the use of rearranged T cell receptor gamma genes as clonal markers. *J Immunol Methods*. Jan. 20, 2006; 308(1-2):1-12.
22. Hadrup S R, Strindhall J, Koligaard T, et al. Longitudinal studies of clonally expanded CD8 T cells reveal a repertoire shrinkage predicting mortality and an increased number of dysfunctional cytomegalovirus-specific T cells in the very elderly. *J Immunol*. Feb. 15, 2006; 176(4):2645-2653.
23. Goronzy J J, Weyand C M. T cell development and receptor diversity during aging. *Curr Opin Immunol*. October 2005; 17(5):468-475.
24. Taub D D, Longo D L. Insights into thymic aging and regeneration. *Immunol Rev*. June 2005; 205:72-93.
25. Baba Y, Kuroiwa A, Uitti R J, Wszolek Z K, Yamada T. Alterations of T-lymphocyte populations in Parkinson disease. *Parkinsonism Relat Disord*. December 2005; 11(8): 493-498.
26. Phillips J A, Brondstetter T I, English C A, Lee H E, Virts E L, Thoman M L. IL-7 gene therapy in aging restores early thymopoiesis without reversing involution. *J Immunol*. Oct. 15, 2004; 173(8):4867-4874.
27. Murphy W J, Durum S K, Longo D L. Role of neuroendocrine hormones in murine T cell development. Growth hormone exerts thymopoietic effects in vivo. *J Immunol*. Dec. 15, 1992; 149(12):3851-3857.
28. Montecino-Rodriguez E, Clark R, Dorshkind K. Effects of insulin-like growth factor administration and bone marrow transplantation on thymopoiesis in aged mice. *Endocrinology*. October 1998; 139(10):4120-4126.

We claim:

1. A method of increasing thymic output in an HIV-negative patient, comprising the steps of (a) identifying a HIV-negative patient who is in need of increased thymic output and (b) supplying an effective amount of antiretroviral agent to the patient such that the patient has an increase in naïve T cells, wherein the patient has idiopathic CD4 lymphocytopenia.

2. The method of claim 1 wherein the patient has received or is receiving immunosuppressive medication.

3. The method of claim 1 wherein the patient has had a bone marrow transplant.

4. The method of claim 1 additionally comprising step (c), wherein step (c) comprises measuring the patient's naïve T cell level.

5. The method of claim 4 wherein step (c) comprises determining TREC number.

6. The method of claim 1 wherein the antiretroviral agent is nelfinavir.

7. The method of claim 6 wherein the nelfinavir is administered at between 1000-2000 mg orally, twice a day for between 15 and 25 days.

8. The method of claim 1 wherein the HIV-negative patient is a human being.

9. The method of claim 1 wherein the increase in TREC is at least 1.2 fold by 21 days of antiretroviral agent treatment.

10. The method of claim 1 wherein the human patient is less than forty years old.

11. The method of claim 1 wherein the human patient has breast cancer.

12. The method of claim 1 additionally comprising the step of sampling the patient's blood before and after antiretroviral therapy and analyzing the blood sample for naïve T-cell levels.

13. The method of claim 12 wherein the increase is at least 1.2 fold.

* * * * *

UNITED STATES PATENT AND TRADEMARK OFFICE
CERTIFICATE OF CORRECTION

| | |
|---|---|
| PATENT NO. | : 8,093,234 B2 |
| APPLICATION NO. | : 11/580359 |
| DATED | : January 10, 2012 |
| INVENTOR(S) | : Badley et al. |

It is certified that error appears in the above-identified patent and that said Letters Patent is hereby corrected as shown below:

IN THE SPECIFICATIONS:

Column 3, line 52 "M" should be -- AA --

Column 5, line 33 "M" should be -- AA --

Signed and Sealed this
Twenty-ninth Day of May, 2012

David J. Kappos
*Director of the United States Patent and Trademark Office*

SEQUENCE LISTING

<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: PCR PRIMERS

<400> SEQUENCE: 1
cacatccctt tcaaccatgc t                                              21

<210> SEQ ID NO 2
<211> LENGTH: 19
<212> TYPE: DNA
<213> ORGANISM: Artificial
<220> FEATURE:
<223> OTHER INFORMATION: PCR PRIMERS

<400> SEQUENCE: 2
gccagctgca gggtttagg                                                 19

<210> SEQ ID NO 3
<211> LENGTH: 30
<212> TYPE: DNA
<213> ORGANISM: Artificial
<220> FEATURE:
<223> OTHER INFORMATION: PCR PRIMERS

<400> SEQUENCE: 3
acacctctgg ttttttgtaaa ggtgcccact                                    30

<210> SEQ ID NO 4
<211> LENGTH: 26
<212> TYPE: DNA
<213> ORGANISM: Artificial
<220> FEATURE:
<223> OTHER INFORMATION: PCR PRIMERS

<400> SEQUENCE: 4
gtgtcaagtc caatctatga catcaa                                         26

<210> SEQ ID NO 5
<211> LENGTH: 19
<212> TYPE: DNA
<213> ORGANISM: Artificial
<220> FEATURE:
<223> OTHER INFORMATION: PCR PRIMERS

<400> SEQUENCE: 5
gcctgcgatt tgcttcaca                                                 19

<210> SEQ ID NO 6
<211> LENGTH: 31
<212> TYPE: DNA
<213> ORGANISM: Artificial
<220> FEATURE:
<223> OTHER INFORMATION: PCR PRIMERS

<400> SEQUENCE: 6
tattatacat cggagccctg ccaaaaaatc a                                   31